(12) United States Patent
Ikemoto (10) Patent No.: US 9,430,833 B2
(45) Date of Patent: Aug. 30, 2016

(54) IMAGE PROCESSING DEVICE AND ENDOSCOPE DEVICE

(71) Applicant: HOYA CORPORATION, Tokyo (JP)

(72) Inventor: Yousuke Ikemoto, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 0 days.

(21) Appl. No.: 14/413,905

(22) PCT Filed: May 14, 2013

(86) PCT No.: PCT/JP2013/063385
§ 371 (c)(1),
(2) Date: Jan. 9, 2015

(87) PCT Pub. No.: WO2014/013778
PCT Pub. Date: Jan. 23, 2014

(65) Prior Publication Data
US 2015/0193929 A1    Jul. 9, 2015

(30) Foreign Application Priority Data

Jul. 17, 2012    (JP) .................................. 2012-158248

(51) Int. Cl.
*G06K 9/00*    (2006.01)
*G06T 7/00*    (2006.01)
(Continued)

(52) U.S. Cl.
CPC ........... *G06T 7/0014* (2013.01); *A61B 1/00009* (2013.01); *A61B 5/061* (2013.01);
(Continued)

(58) Field of Classification Search
USPC ......... 382/100, 103, 128–134, 162–173, 181, 382/194, 199, 219, 232, 254–250, 274, 276, 382/291, 299, 305, 312; 600/160; 378/4, 378/21; 348/65, 71
See application file for complete search history.

(56) References Cited

U.S. PATENT DOCUMENTS 7,283,858 B2 * 10/2007 Sendai ................. A61B 5/0071
600/160
7,289,140 B2    10/2007 Kobayashi
(Continued)

FOREIGN PATENT DOCUMENTS

CN    101677753    3/2010
CN    101803899    8/2010
(Continued)

OTHER PUBLICATIONS

Office Action in U.S. Appl. No. 14/415,378 dated Jan. 16, 2015.
(Continued)

*Primary Examiner* — Seyed Azarian
(74) *Attorney, Agent, or Firm* — Greenblum & Bernstein P.L.C.

(57) ABSTRACT

An image processing device, comprising an obtaining means that obtains color endoscopic image data, a color space conversion means that converts a color space of the color endoscopic image data to an HSI color space based on hue, saturation and intensity or an HSV color space based hue, saturation and a value, a lesion pixel judgment means that judges, for each of pixels constituting a color endoscopic image, whether or not each pixel is a lesion portion based on the hue and the saturation, an overlay processing means that executes an overlay process which changes a color of the pixel judged to be the lesion portion by the lesion pixel judgment means, and an overlay image display means that displays an overlay image obtained by subjecting the color endoscopic image to the overlay process.

14 Claims, 9 Drawing Sheets

(51) Int. Cl.
*A61B 1/00* (2006.01)
*A61B 5/06* (2006.01)
*G06T 7/40* (2006.01)
*A61B 1/06* (2006.01)

(52) U.S. Cl.
CPC .............. *G06T 7/0012* (2013.01); *G06T 7/408* (2013.01); *G06T 2207/10024* (2013.01); *G06T 2207/10068* (2013.01); *G06T 2207/20172* (2013.01); *G06T 2207/30028* (2013.01); *G06T 2207/30096* (2013.01)

(56) References Cited

U.S. PATENT DOCUMENTS

| | | | |
|---|---|---|---|
| 7,938,771 B2 | 5/2011 | Homan et al. | |
| 8,225,209 B2 | 7/2012 | Shigemori | |
| 8,274,558 B2 | 9/2012 | Takayama | |
| 8,452,092 B2 | 5/2013 | Sasaki | |
| 8,675,058 B2 * | 3/2014 | Donomae | A61B 1/00105 348/71 |
| 8,743,189 B2 * | 6/2014 | Kitamura | A61B 1/041 348/65 |
| 8,837,821 B2 | 9/2014 | Hirota et al. | |
| 2002/0105505 A1 | 8/2002 | Sendai | |
| 2002/0177779 A1 | 11/2002 | Adler et al. | |
| 2004/0155957 A1 | 8/2004 | Kobayashi | |
| 2006/0087557 A1 | 4/2006 | Donomae et al. | |
| 2007/0161858 A1 | 7/2007 | Homan et al. | |
| 2009/0309961 A1 | 12/2009 | Miyashita | |
| 2010/0007724 A1 | 1/2010 | Takayama | |
| 2010/0115469 A1 | 5/2010 | Shigemori | |
| 2010/0158330 A1 * | 6/2010 | Guissin | G06K 9/00369 382/128 |
| 2010/0208047 A1 | 8/2010 | Kitamura | |
| 2011/0075901 A1 | 3/2011 | Nakamura | |
| 2011/0176730 A1 | 7/2011 | Sasaki | |
| 2011/0242301 A1 | 10/2011 | Morita | |
| 2011/0311133 A1 | 12/2011 | Hirota et al. | |
| 2014/0320620 A1 * | 10/2014 | Ikemoto | A61B 1/00009 348/71 |

FOREIGN PATENT DOCUMENTS

| | | |
|---|---|---|
| CN | 102243762 | 11/2011 |
| EP | 1839558 | 10/2007 |
| EP | 1994878 | 11/2008 |
| EP | 2096859 | 9/2009 |
| EP | 2156784 | 2/2010 |
| EP | 2386999 | 11/2011 |
| EP | 2517614 | 10/2012 |
| JP | 2-114931 | 4/1990 |
| JP | 3-4832 | 1/1991 |
| JP | 2002-172082 | 6/2002 |
| JP | 2004-154176 | 6/2004 |
| JP | 2004-236952 | 8/2004 |
| JP | 2006-142002 | 6/2006 |
| JP | 2009-106424 | 5/2009 |
| JP | 2009-297365 | 12/2009 |
| JP | 2010-36017 | 2/2010 |
| JP | 2010-115243 | 5/2010 |
| JP | 2010-172673 | 8/2010 |
| JP | 2010-187756 | 9/2010 |
| JP | 2011-143100 | 7/2011 |
| JP | 2011-182993 | 9/2011 |
| JP | 2011-218090 | 11/2011 |
| JP | 2011-234931 | 11/2011 |
| JP | 2011-255006 | 12/2011 |
| WO | 2008/146447 | 12/2008 |
| WO | 2011/096279 | 8/2011 |

OTHER PUBLICATIONS

Office Action issued in China Counterpart Patent Appl. No. 201380038083.7, dated Feb. 25, 2016, along with an English translation thereof.
U.S. Appl. No. 14/415,378 to Yousuke Ikemoto et al., filed Jan. 16, 2015.
International Preliminary Report on Patentability in PCT/JP2013/063385, mail date is Jan. 29, 2015, together with an English translation thereof.
International Search Report in PCT/JP2013/063385, mail date is Jun. 25, 2013, together with an English translation thereof.
Search Report issued by E.P.O. patent office in E.P.O. Patent Application No. 13819790.0, dated Mar. 23, 2016.
Office Action issued in China Counterpart Patent Appl. No. 201380037982.5, dated Mar. 16, 2016, along with an English translation thereof.
Office Action issued in Japan Counterpart Patent Appl. No. 2012-158248, dated Feb. 15, 2016, along with an English translation thereof.
Search Report issued by EPO patent office in EPO Patent Application No. 13819629.0, dated Apr. 1, 2016.
International Search report, with English language translation, in PCT/JP2013/063384, mail date is Jun. 18, 2013.
International Preliminary Report on Patentability, with Written Opinion and English language translation, in PCT/JP2013/063384, mailed date Jan. 29, 2015.

* cited by examiner

IMAGE PROCESSING DEVICE AND ENDOSCOPE DEVICE

TECHNICAL FIELD

The present invention relates an image processing device for endoscopic diagnosis and a medical endoscope device provided with the image processing device, and particularly to a device having the function of obtaining and displaying information on a lesion portion based on color information of a color endoscopic image.

BACKGROUND ART

In general, a lesion portion shows a color different from a color of a normal mucous membrane tissue. Thanks to enhancement of the performance of a color endoscope device, identification of a lesion portion of which color is slightly different from a color of a normal tissue has become possible. However, in order to become able to precisely identify a lesion portion from a normal tissue based on a slight difference in color on an endoscopic image, an operator needs to be trained under expert's instruction for a long period of time. Furthermore, even for a practiced operator, it is not easy to identify a lesion portion based on a slight difference in color, and therefore careful work was required. For this reason, an electronic endoscope device having the function of executing a color conversion process for highlighting a difference in color with respect to endoscopic image data captured using white light, in order to ease identification of a lesion portion, is proposed, for example, in Japanese Patent Provisional Publication No. 2009-106424A (hereafter, referred to as patent document 1).

SUMMARY OF THE INVENTION

It can be said that an image generated by an electronic endoscope described in patent document 1 is easy to identify a lesion portion and the like in comparison with a normal endoscopic image. However, change in color at a boundary between a normal mucous membrane and a lesion portion and the like is continuous, and a difference in color between a normal mucous membrane and a lesion portion becomes very small depending on the type of disease. For this reason, even when the electronic endoscope device described in patent document 1 is used, the problem that identification of a lesion portion and the like is difficult is not resolved. Furthermore, even when the electronic endoscope device described in the patent document 1 is used, judgment on whether or not it is a lesion portion is eventually left to an operator's subjectivity based on color perception which is an ambiguous sense, and therefore it is impossible to obtain a diagnostic result having objectivity and reproducibility (which does not depend on the operator's skill).

According to an embodiment of the invention, there is provided an image processing device, comprising an obtaining means that obtains color endoscopic image data, a color space conversion means that converts a color space of the color endoscopic image data to an HSI color space based on hue, saturation and intensity or an HSV color space based hue, saturation and a value, a lesion pixel judgment means that judges, for each of pixels constituting a color endoscopic image, whether or not each pixel is a lesion portion based on the hue and the saturation, an overlay processing means that executes an overlay process which changes a color of the pixel judged to be the lesion portion by the lesion pixel judgment means, and an overlay image display means that displays an overlay image obtained by subjecting the color endoscopic image to the overlay process.

With this configuration, since the judgment on the lesion portion is made in the HSV color space where the difference between the lesion portion and the normal portion clearly appears, is becomes possible to make an accurate judgment on the lesion portion and the normal portion. Furthermore, by displaying the overlay image in which the color of the pixel of the lesion portion has been changed, it becomes possible for the operator to more clearly identify the lesion portion and thereby it becomes possible to conduct a diagnosis with high accuracy and reproducibility.

The lesion pixel judgment means may judge whether or not each pixel is a pixel of the lesion portion, for each of a plurality of types of lesions, and the overlay image display means may change a color of the pixel of the lesion portion depending on a type of lesion.

With this configuration, it becomes possible to conduct a diagnosis more appropriately for a disease accompanied by expression of a plurality of types of lesion, such as an inflammatory bowel disease.

In the above described image processing device, the overlay processing means may add a predetermined value corresponding to a type of lesion to a pixel value of a pixel judged to be the lesion portion.

With this configuration, lesion portions of different types are displayed according to their colors, it becomes possible to recognize intuitively and accurately the more detailed information on a state of a disease.

In the above described image processing device, the overlay image display means may display concurrently the color endoscopic image and the overlay image.

With this configuration, identification of a lesion portion photographed on the color endoscopic image is eased.

In the above described image processing device, the image processing device may further comprise an effective pixel judgment means that judges, for each of the pixels constituting the color endoscopic image, whether or not each pixel is effective by judging whether or not a pixel value is within a predetermined range, and the lesion pixel judgment means may judge whether each pixel is a pixel of the lesion portion for the pixel judged to be effective by the effective pixel judgment means.

With this configuration, by excluding the non-effective pixel (e.g., a pixel with a low accuracy of a pixel value, such as a case of an extremely high pixel value or an extremely low pixel value) from a judgment target, the more accurate identification of the lesion portion can be achieved.

In the above described image processing device, the image processing device may further comprise a tone enhancement means that executes a tone enhancement process applying a non-linear gain to a pixel value so that a dynamic range near a boundary of a region of the pixel value for which the pixel is judged to be the lesion portion is broadened, and the lesion pixel judgment means may make a judgment based on the pixel value after the tone enhancement process.

With this configuration, a dynamic range near a boundary (a threshold value) of judgment on a lesion portion is widened, it becomes possible to conduct the more precise judgment on a lesion portion.

In the above described image processing device, the color endoscopic image data may be converted into the HSI color space or the HSV color space after being subjected to the tone enhancement process in the RGB color space.

In the above described image processing device, the tone enhancement means may execute the tone enhancement process while applying different gain curves to intensity values of respective primary colors of R, G and B.

With this configuration, it becomes possible to conduct the more accurate judgment on a lesion portion by the tone enhancement process having a high degree of freedom.

In the above described image processing device, the lesion may include an inflammation and an ulcer in an inflammatory bowel disease.

According to a configuration of an embodiment of the invention, there is provided an endoscope device, comprising the above described image processing device, and an endoscope that generates the color endoscopic image data and outputs the color endoscopic image data to the image processing device.

As described above according to the embodiment of the invention, it becomes possible to conduct the accurate identification between a lesion portion and a normal portion.

EMBODIMENTS FOR CARRYING OUT THE INVENTION

In the following, an embodiment of the invention is explained in detail with reference to the accompanying drawings.

Figure 1:
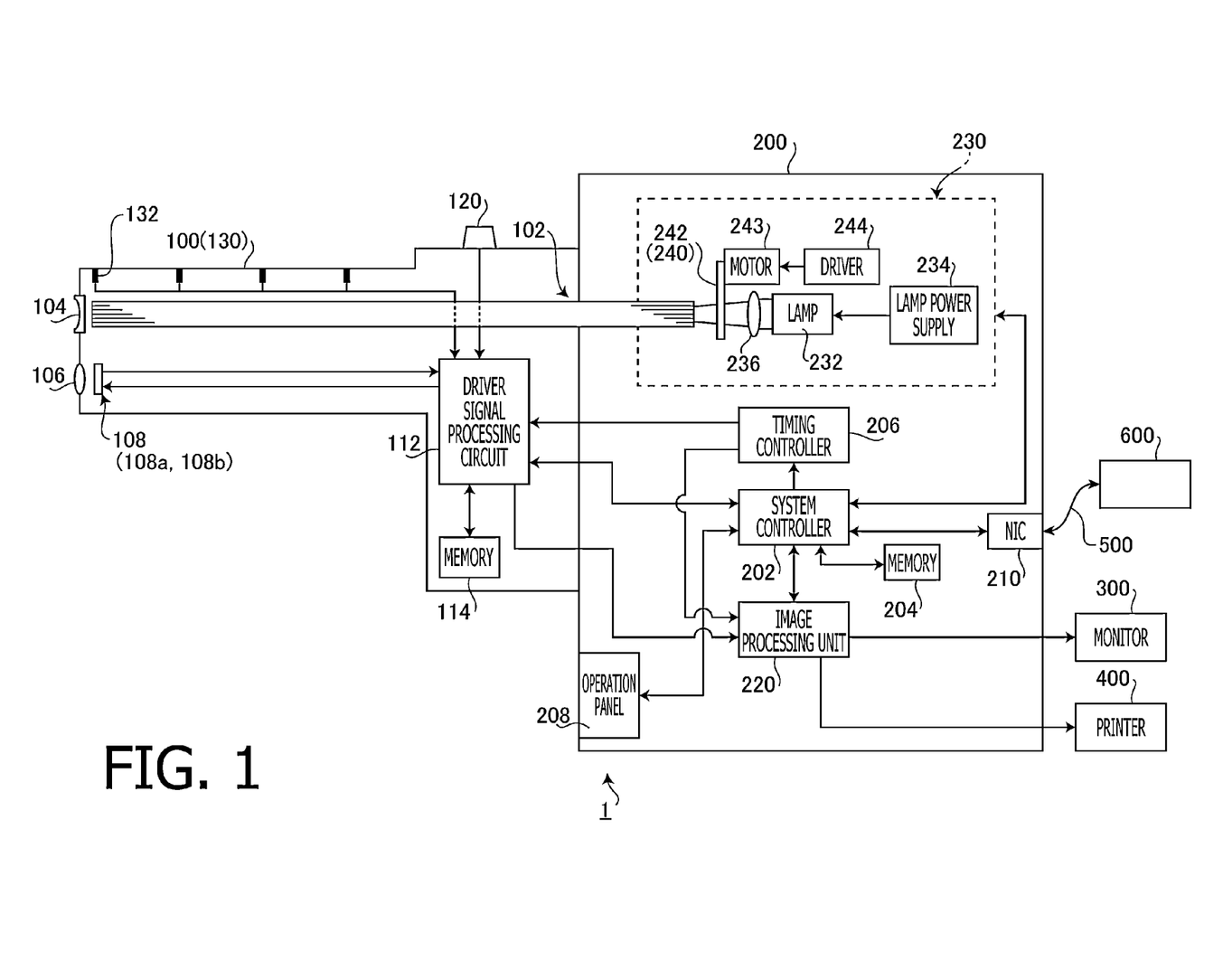
FIG. 1 is a block diagram illustrating a general configuration of an electronic endoscope device according to an embodiment of the invention.

FIG. 1 is a block diagram illustrating a general configuration of an electronic endoscope device 1 according to the embodiment of the invention. As shown in FIG. 1, the electronic endoscope device 1 according to the embodiment includes an electronic scope 100, a processor 200 for an electronic endoscope, a monitor 300 and a printer 400.

The processor 200 for an electronic endoscope includes a system controller 202 and a timing controller 206. The system controller 202 executes various programs stored in a memory 204 and totally controls the entire electronic endoscope device 1. Further, the system controller 202 changes various settings of the electronic endoscope device 1 in accordance with an instruction from a user (an operator or an assistant) input to an operation panel 208. The timing controller 206 outputs clock pulses for adjusting operation timings of each part to various circuits in the electronic endoscope device 1.

Further, the processor 200 for an electronic endoscope includes a light source 230 which supplies illumination light being a white light beam to an LCB (Light Carrying Bundle) 102 of the electronic scope 100. The light source 230 includes a lamp 232, a lamp power supply 234, a condenser lens 236 and a dimmer control device 240. The lamp 232 is a high luminance lamp which emits illumination light while being supplied drive power from the lamp power supply 234, and, for example, a Xenon lamp, a metal-halide lamp, a mercury lamp or a halogen lamp is used. The illumination light emitted by the lamp 232 is converged by the condenser lens 236, and is guided to the LCB 102 via the dimmer control device 240.

The dimmer control device 240 is a device which adjusts the light amount of the illumination light guided to the LCB 102 based on control by the system controller 202, and includes an aperture stop 242, a motor 243 and a driver 244. The driver 244 generates a driving current for driving the motor 243, and supplies the driving current to the motor 243. The aperture stop 242 is driven by the motor 243, and changes the aperture through which the illumination light proceeds, and thereby controls the light amount of the illumination light passing through the aperture.

The illumination light guided to the LCB 102 from an entrance face propagates through the inside of the LCB 102, is emitted from an exit face of the LCB 102 disposed at a tip part of the electronic scope 100, and illuminates a subject via a light distribution lens 104. Light reflected from the subject forms an optical image on a light-receiving surface of a solid state image pickup device 108 via an objective lens 106.

The solid state image pickup device 108 is, for example, a single-chip color CCD (Charge Coupled Device) image sensor having various filters, such as, an IR (Infra Red) cut filer 108a and a bayer array color filter 108b, disposed on the light-receiving surface thereof, and generates an image-capturing signal of each of three primary colors responsive to the optical image converged on the light receiving surface. The generated image-capturing signal is amplified by a driver signal processing circuit 112 provided in a connection part of the electronic scope 100, and then is converted into an image signal composed of a luminance signal Y and color difference signals Cb and Cr. The image signal converted into the luminance signal Y and the color difference signals Cb and Cr is further converted into a digital signal and then is transmitted to an image processing unit 220 of the processor 200 for an electronic endoscope. Further, the driver signal processing circuit 112 reads out unique information unique to the electronic scope 100 by accessing the memory 114. The unique information of the electronic scope 100 recorded in the memory 114 includes, for example, the number of pixels and the sensitivity of the solid state image pickup device 108, operable frame rates and the like. The driver signal processing circuit 112 outputs the unique information read from the memory 114 to the system controller 202.

The system controller 202 executes various calculations based on the unique information of the electronic scope 100, and generates a control signal. Using the generated control signal, the system controller 202 controls the operations and timings of the various circuits in the processor 200 for an electronic endoscope so that processes suitable for the electronic scope 100 connected to the processor 200 for an electronic endoscope are executed.

The timing controller 206 supplies clock pulses to the driver signal processing circuit 112 and the image processing unit 220 in accordance with timing control by the system controller 202. The driver signal processing circuit 112 drives and controls the solid state image pickup device 108 at timings in synchronization with a frame rate of video processed by the processor 200 for an electronic endoscope side, in accordance with the clock pulses supplied from the timing controller 206.

The image processing unit 220 of the processor 200 for an electronic endoscope generates a video signal for monitor representation of an endoscopic image or the like based on the image signal transmitted from the driver signal processing circuit 112 of the electronic scope 100, under control of the system controller 202, and outputs the video signal to the monitor 300. The operator observes or treats, for example, an inside of a digestive tube, while checking the endoscopic image displayed on the monitor 300.

The processor 200 for an electronic endoscope is connected to a server 600 via a NIC (Network Interface Card) 210 and a network 500. The processor 200 for an electronic endoscope obtains, from the server 600, information concerning endoscopic examination (e.g., electronic medical record of a patient or information on an operator) and displays the information on the monitor 300 or the operation panel 208. Further, the processor 200 for an electronic endoscope transmits endoscopic examination results (endoscopic image data, examination conditions, image analysis results which are described later, an operator's opinion or the like) to the server 600 to cause the server 600 to store the endoscopic examination results.

Further, the electronic endoscope device 1 includes the function of recording still images of a plurality of endoscopic images in association with information on captured portions (i.e., positions (insertion lengths) of the tip part of the electronic scope 100 at the time of image capturing). On an outer circumferential surface of an insertion unit 130 of the electronic scope 100, a plurality of optical sensors 132 are provided at constant intervals (e.g., intervals of 5 centimeters) in the length direction. The optical sensor 132 is a light-receiving device, such as a photodiode, and detects external light (room lighting of a room in which the endoscopic examination is being performed). The optical sensors 130 provided on a part of the insertion unit 130 inserted into the digestive tube do not detect the external light, and the optical sensors 132 provided on a part of the insertion unit 130 not inserted into the digestive tube detect the external light. Therefore, by judging that the length of distribution of the optical sensors not detecting the light is the length of the insertion unit 130 inserted into the inside of the digestive tube, it becomes possible to obtain information concerning the position of the tip part of the electronic scope 100 (the insertion length). The optical sensors 132 are connected to the driver signal processing circuit 112, and transmit sensor signals indicating the amounts of the detected light to the driver signal processing circuit 112. The driver signal processing circuit 112 calculates the position (the insertion length) Pos of the tip part of the electronic scope 100 based on the sensor signals from the optical sensors 132.

When an operation for instructing obtaining of a still image is conducted with respect to the operation unit 120 of the electronic scope 100, an operation signal is transmitted from the operation unit 120 to the driver signal processing circuit 112. When the system controller 202 obtains the operation signal for obtaining a still image from the operation unit 120, the system controller 202 transmits an instruction for obtaining a still image to the image processing unit 220 together with the current position information (the insertion length) Pos of the tip part of the electronic scope 100. As a result, in the image processing unit 220, a still image of an endoscopic observation image is recorded while being associated with the position information Pos of the electronic scope 100 at the time of image capturing. Details about a process in which the image processing unit 220 records a still image are described later.

Figure 2:
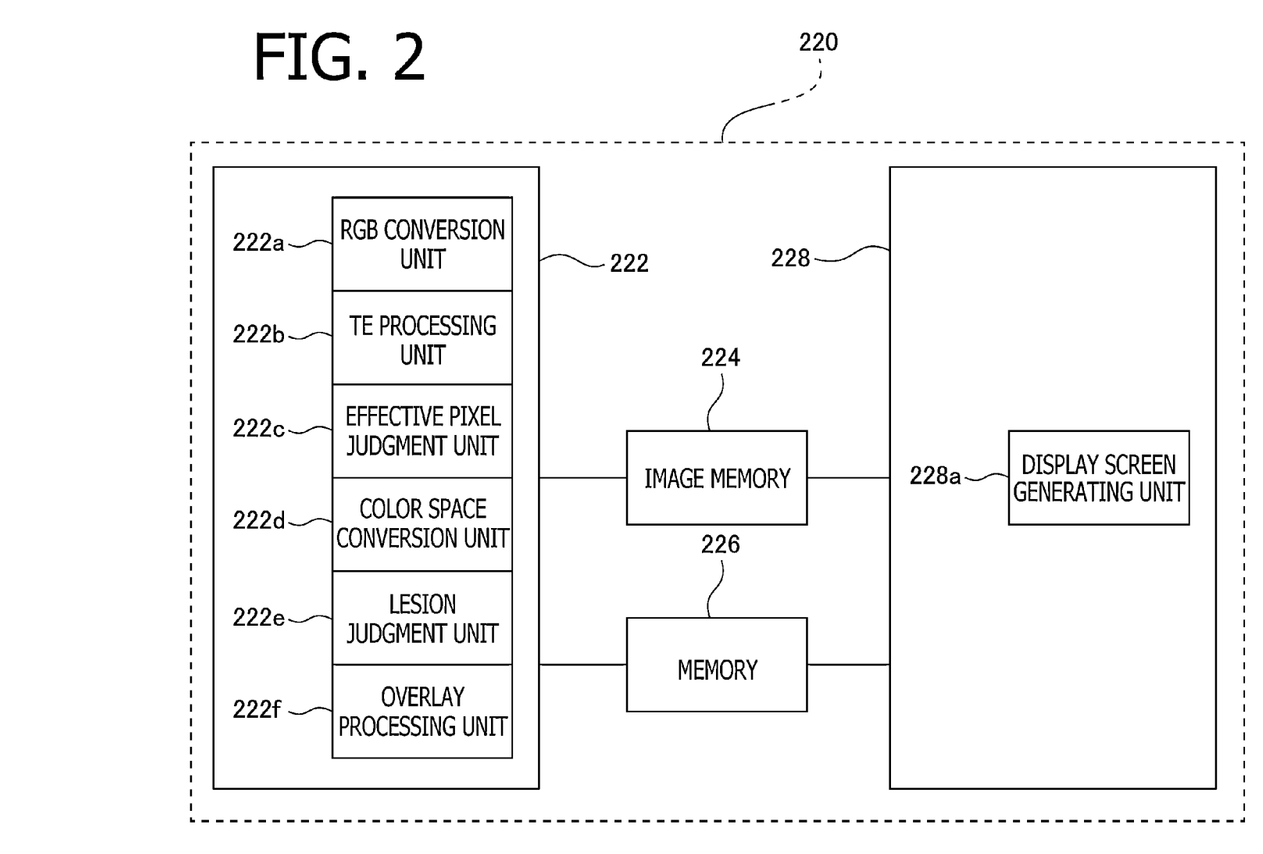
FIG. 2 is a block diagram illustrating a general configuration of an image processing unit according to the embodiment of the invention.

FIG. 2 is a lock diagram illustrating a general configuration of the image processing unit 220. The image processing unit 220 includes a first image processing circuit 222, an image memory 224, a memory 226 and a second image processing circuit 228. The first image processing circuit 222 executes various types of image processing for the image signal from the driver signal processing circuit 112, and outputs the signal to the image memory 224.

As shown in FIG. 2, the first image processing circuit 222 includes an RGB conversion unit 222a, a TE processing unit 222b, an effective pixel judgment unit 222c, a color space conversion unit 222d, a lesion judgment unit (a threshold processing unit) 222e and an overlay processing unit 222f. Further, the second image processing circuit 228 includes a display screen generating unit 228a. Concrete processes executed by each of the units of the first image processing circuit 222 and the second image processing circuit 228 are explained later.

Figure 3:
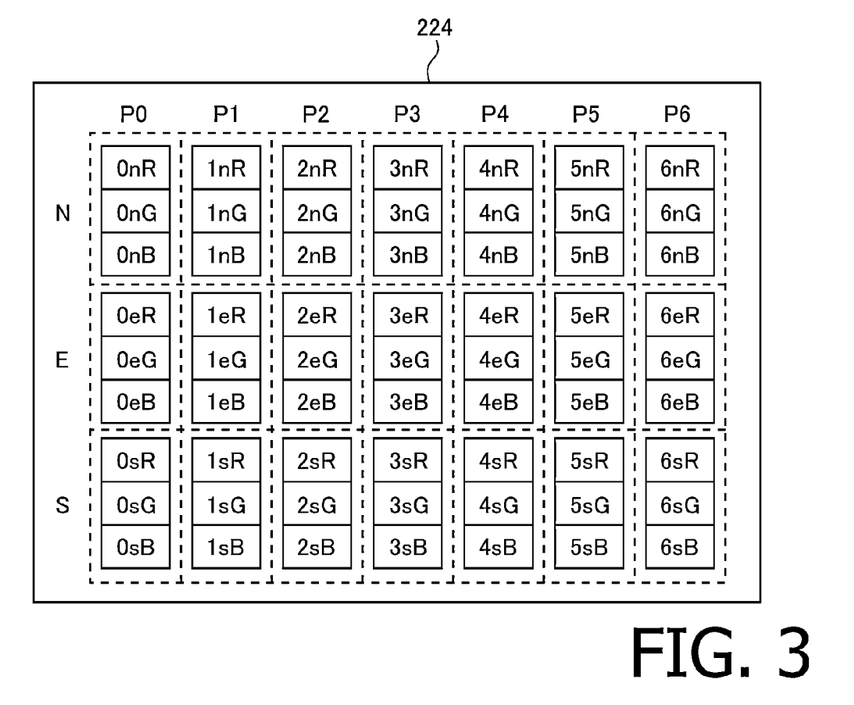
FIG. 3 is a diagram illustrating a general configuration of a memory area of an image memory 224.

FIG. 3 illustrates a general configuration of a memory area provided in the image memory 224. In the image memory 224 according to the embodiment, seven memory are groups Pk (k=0 to 6) are provided. Each memory area group Pk includes normal image memory areas KnR, KnG, KnB (k=0 to 6) respectively storing three primary color signals R, G, B of normal observation image data N, tone enhanced image memory areas KeR, KeG, KeB (k=0 to 6) respectively storing primary color signals R', G', B' of tone enhanced image data E generated by a TE process S3 which is described later, and overlay image memory areas KsR, KsG, KsB (k=0 to 6) respectively storing three primary colors R", G", B" of overlay image data S generated by an overlay process S7 which is described later. That is, the image memory 224 is able to store a maximum of seven sets of the normal observation image data N, the tone enhanced image data E and the overlay image data S. The image memory 224 is configured to store the image data output by the first image processing circuit 222 (the normal observation image data N, the tone enhanced image data E or the overlay image data S) in one of the memory area groups P0 to P6 in accordance with control of the system controller 202. It should be noted that the memory area P0 is overwritten with the image data sequentially output from the first image processing circuit 222, so that the image data constituting a real time video image is held thereon. On the other hand, to the memory areas P1 to P6, the image data output from the first image processing circuit 222 is written only when an instruction is inputted from the system controller 202. That is, the image memory 224 is able to record a maximum of six still images.

Figure 4:
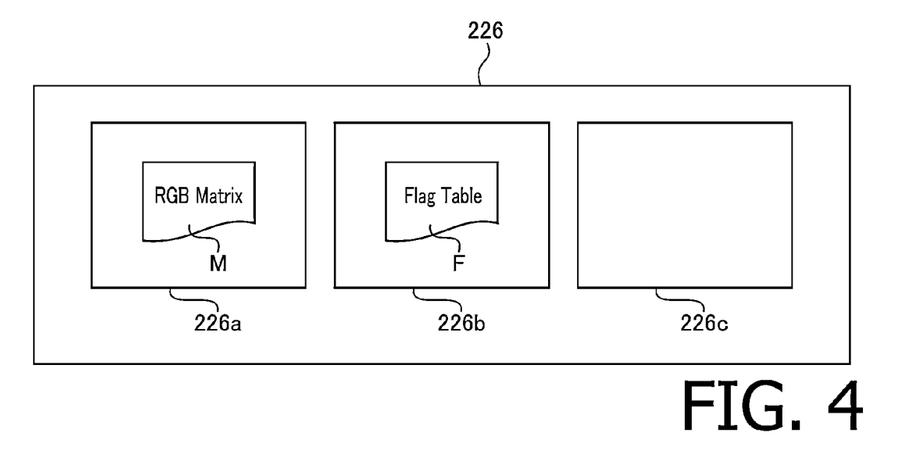
FIG. 4 is a diagram illustrating a general configuration of a memory area of a memory 226.

FIG. 4 illustrates a general configuration of a memory area provided in the memory 226. The memory 226 includes an RGB matrix memory area 226a, a flag memory area 226b, and a setting information memory area 226c. In a RGB matrix memory area 226a, an RGB conversion matrix coefficient M used in an RGB conversion process S1 which is described later is stored. In the flag memory area 226b, a flag table F used for a process in the first image processing circuit 222 is stored. The flag table F is a numeric value table constituted by a flag f(x, y) indicating an analysis result concerning each pixel (x, y) constituting the image data. In the setting information memory area 226c, various types of settings used for a process in the image processing unit 220 are stored.

The memory area group Pk is associated with the position information (the insertion length) Pos of the tip part of the electronic scope 100. Specifically, the memory area group P1 corresponds to a range of the insertion length Pos of a deepest portion (e.g., a portion near a right colic flexure of a transverse colon) in an examination area, and the insertion length Pos becomes shorter as the value of k increases. The memory area group P6 corresponds to a range of the insertion length Pos corresponding to an area around a rectum. That is, when still images are obtained while drawing the insertion unit 130 of the electronic scope 100 from the deepest portion of the examination area, the still images are recorded in the memory areas of k=1 to 6 in the order that the still images are obtained. The setting information that defines the correspondence between the position information Pos and the memory are group Pk (k=1 to 6) is recorded in the setting information memory area 226c. The memory area group Pk in which the image data is recorded is determined depending on the position information Pos (the position of the tip part of the electronic scope 100 at the time of image capturing) of the image data.

The second image processing circuit 228 generates the video signal for monitor representation using the image signal stored in the image memory 224, and outputs the video signal to the monitor 300.

Figure 5:
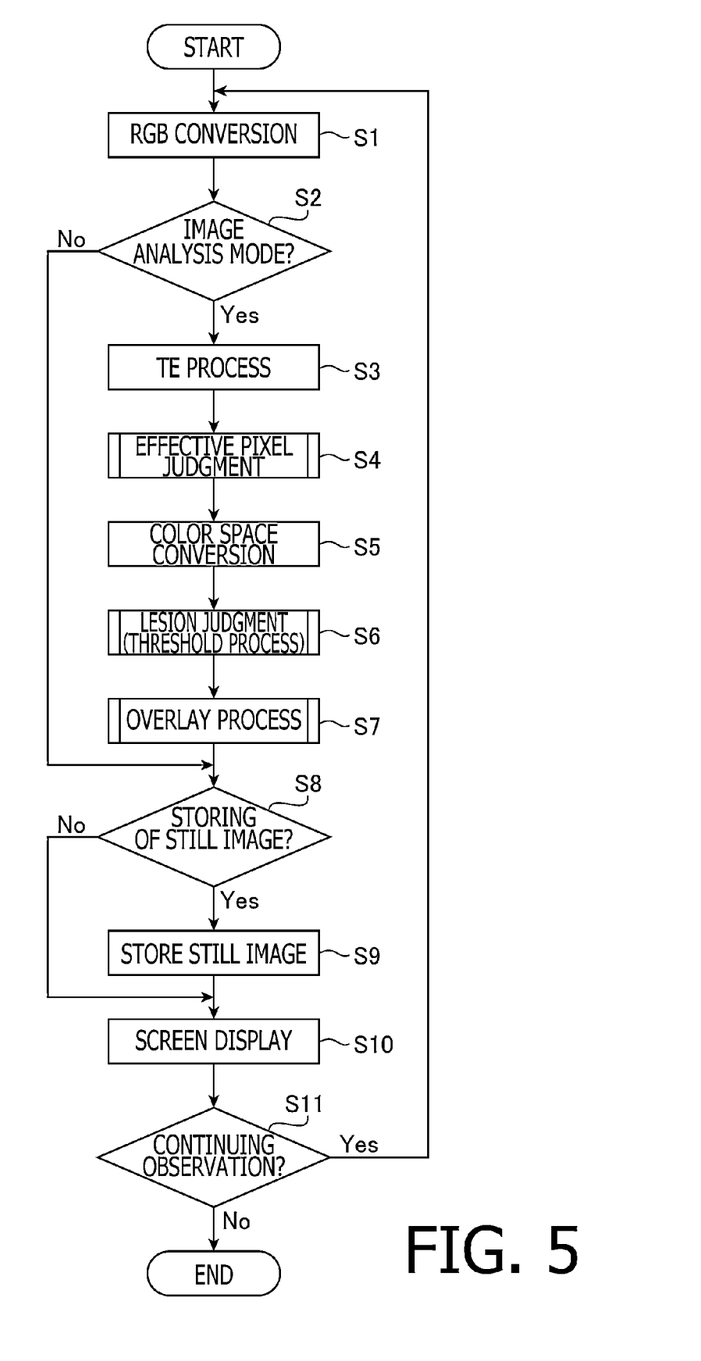
FIG. 5 is a flowchart illustrating a sequence of a process executed by the image processing unit.

Next, details about a process executed by the image processing unit 220 are explained. FIG. 5 is a flowchart illustrating the sequence of the process executed by the image processing unit 220. When the process of the image processing unit 220 starts, first the RGB conversion process S1 is executed by the RGB conversion circuit 222a of the first image processing circuit 222. In the RGB conversion process S1, the RGB conversion unit 222a amplifies respectively the luminance signal Y and color difference signals Cb and Cr transmitted from the driver signal processing circuit 112, and then converts the signals to the three primary color signals R, G, B. The RGB conversion process S1 is executed using the RGB conversion matrix coefficient M stored in the RGB matrix memory area 226a. The RGB conversion matrix coefficient M has been set in advance in accordance with the spectral property of the illumination light used for image capturing, and correction of the spectral property of the illumination light is executed concurrently with the conversion in a signal format from the Y, Cr, Cb signals to the R, G, B signals. Further, when the RGB conversion process S1 is finished, the three primary color signals R, G, B of the generated normal observation image data N are output to the image memory 224, and are stored respectively in the normal image memory areas 0nR, 0nG, 0nB.

Next, it is determined whether the mode is set to the image analysis mode (S2). The image analysis mode according to the embodiment of the invention is an operation mode in which color information (in particular, hue and saturation) is analyzed for each pixel of the image data, and whether it is a pixel of a lesion portion is judged based on a predetermined judgment criteria from an analysis result of the color information, and the pixel of the lesion portion is displayed in a discriminating manner. The type of lesion to be judged can be selected depending on content of the examination. In an example explained below, pixels in color regions respectively specific to observation images of an ulcer (a white lesion including a white moss or mucous) which is a lesion of inflammatory bowel disease (IBD) and inflammation (a red coloration lesion including an edema or hemorrhagic) are extracted, and are displayed in a discriminating manner.

The electronic endoscope device 1 according to the embodiment is configured to operate in two operation modes including the image analysis mode and the normal observation mode. The operation mode is changed by a user operation to the operation unit 120 of the electronic scope 100 or the operation panel 208 of the processor 200 for an electronic endoscope. When the operation mode is set to the normal observation mode (S2: No), the process proceeds to S9.

Figure 6:
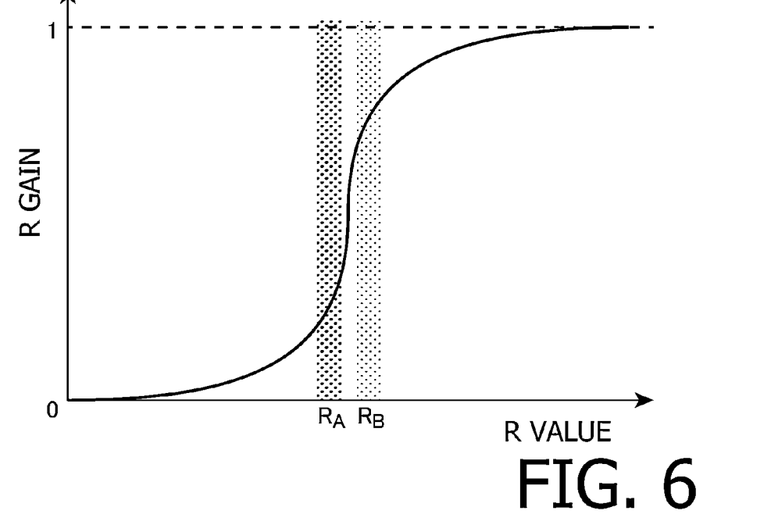
FIG. 6 is an example of a gain curve used for a TE process.

When the image analysis mode is selected (S2: Yes), next the TE process S3 by the tone enhancement (TE) processing unit 222b is executed. The TE process S3 is a process in which, in order to enhance the judgment accuracy of lesion, the gain adjustment for giving a non-linear gain to each of the primary color signals R, G, B is executed, and the dynamic range around a color region (in particular, a boundary portion) specific to the lesion to be judged is substantially widened, and the effective resolution for color representation is enhanced. Specifically, in the TE process S3, a process where a monotonically increasing non-linear gain as shown in FIG. 6 is given to each of the primary color signals R, G, B to obtain the primary color signals R', G', B' (the tone enhanced image data E) is executed. For example, when a boundary region $R_A$ denotes mapping of a boundary of a color region specific to an ulcer to R space and a boundary region $R_B$ denotes mapping of a boundary of a color region specific to inflammation to R space, the inclination of a gain curve becomes most steep around the boundary regions $R_A$ and $R_B$. By providing a gain in accordance with such a gain curve, it becomes possible to widen the substantial dynamic range of the primary color signal R' (the signal obtained by subjecting the primary signal R to the TE process S3) around the boundary regions $R_A$ and $R_B$, and thereby it becomes possible to execute the threshold judgment more precisely.

Here, different gain adjustments may be executed for the primary color signals R, G, B, respectively. Furthermore, a process in which the same non-liner gain is given to the primary color signals G, B and a different non-linear gain is given to the primary color signal R may be performed. Further, the three primary signals R', G', B' (the tone enhanced image data E) generated by the TE process S3 are output to the image memory 224, and are stored in the tone enhanced image memory areas 0eR, 0eG 0eB, respectively.

Through the TE process S3, an inflammation portion changes in color to red, an ulcer portion changes in color to white, and a normal portion changes in color to green. Therefore, when the tone enhanced image data E generated by the TE process S3 is displayed on the monitor 300, it becomes possible to visually recognize a lesion portion (an inflammation portion or an ulcer portion) easily relative to the normal observation image data N.

Figure 7:
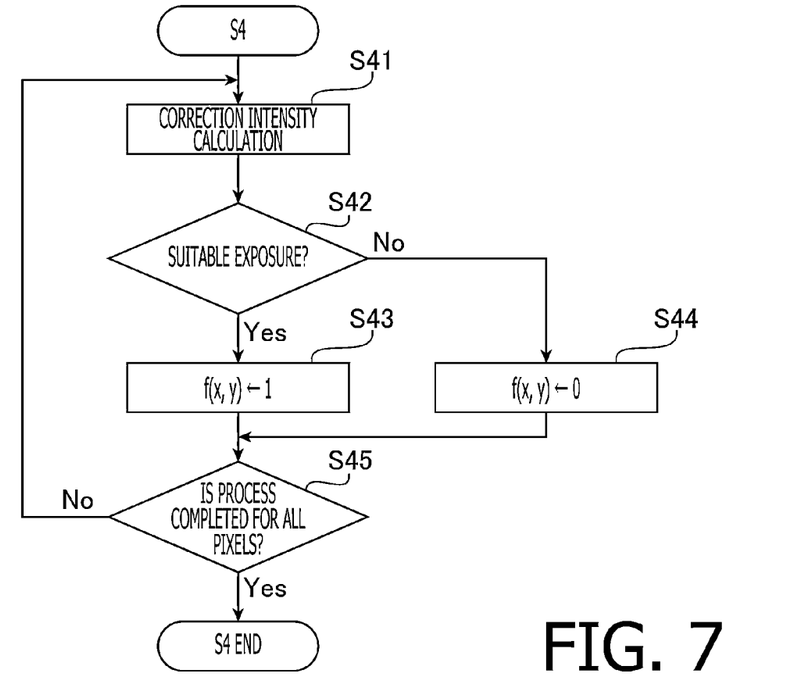
FIG. 7 is a flowchart illustrating a sequence of an effective pixel judgment process.

When the TE process S3 is completed, next an effective pixel judgment process S4 by the effective pixel judgment unit 222c is executed for the tone enhanced image data E. FIG. 7 is a flowchart illustrating the sequence of the effective pixel judgment process S4. The effective pixel judgment process S4 shown in FIG. 7 is executed sequentially for all the pixels (x, y) constituting the image data. In the effective pixel judgment process S4, first a correction intensity int(x, y) is calculated according to the following expression 1 from the primary color signals R'(x, y), G'(x, y), B'(x, y), for each pixel (x, y) (S41).

$$int(x,y)=0.3*R'(x,y)+0.59*G'(x,y)+0.11*B'(x,y) \quad \text{(Expression 1)}$$

The value of the calculated correction intensity (x, y) is used for a suitable exposure judgment S42. Further, as can be seen from the expression 1, the correction intensity int(x, y) is not obtained as a simple average of the primary color signals R'(x, y), G'(x, y), B'(x, y), but is obtained as a weighted average based on a relative luminous efficiency property of a human (an operator).

Next, the suitability of exposure (whether or not it is an exposure level required for image analysis) is judged based on the correction intensity int(x, y) and the primary color signals R'(x, y), G'(x, y), B'(x, y) of the tone enhanced image data E calculated in the process S41 (S42). In the suitable exposure judgment process S42, it is judged to be a suitable exposure (S42: Yes) when at least one of the following two conditions (the expression 2 and the expression 3) is satisfied. It should be noted that the upper limit of the correction intensity int(x, y) is defined by the expression 2, and the lower limit of each of the primary color signals R'(x, y), G'(x, y), B'(x, y) is defined by the expression 3.

$$int(x,y)<235 \qquad \text{(Expression 2)}$$

$$\text{Max}\{R'(x,y),G'(x,y),B'(x,y)\}>20 \qquad \text{(Expression 3)}$$

When, for the pixel (x, y), the expressions (2) and (3) are satisfied and it is judged to be the suitable exposure (S42: Yes), the effective pixel judgment unit 222c changes the value of the flag (x, y) corresponding to the pixel (x, y) of the flag table F stored in the flag memory area 226b of the memory 226 to "1" (S43). The flag f (x, y) takes a value of one of 0 to 3. The following is the definition of each of the flag values.

0: Invalid image data
1: No lesion (Normal) or Non-judgment on lesion (image data effective)
2: Lesion A (Inflammation)
3: Lesion B (Ulcer)

When none of the expression 2 and the expression 3 is satisfied and the exposure is judged to be not suitable in the suitable exposure judgment S42 (S42: No), the effective pixel judgment unit 222c changes the value of the flag f(x, y) of the flag table F to "0" (S44).

Next, in the process S45, it is judged whether the process is completed for all the pixels (x, y). Until the process is completed for all the pixels (x, y), the above described processes S41 to S45 are repeated.

When the effective pixel judgment process S4 is completed, next a color space conversion process S5 is executed by the color space conversion unit 222d. The color space conversion process S5 is a process where the tone enhanced image data in the RGB space defined by the RGB three primary colors is converted into image data in HSI (Hue-Saturation-Intensity) space defined by three elements of Hue, Saturation and Intensity. Specifically, in the color space conversion process S5, the primary color signals R'(x, y), G'(x, y), B'(x, y) of each pixel (x, y) of the tone enhanced image data E are converted into hue H(x, y), saturation S(x, y), intensity I(x, y). Since the intensity I(x, y) is not used in the following process in this embodiment, calculation for the intensity I(x, y) is not executed and only the hue H(x, y) and the saturation S(x, y) are calculated so that the processing efficiency is enhanced.

Data of a pixel whose exposure is short or excessive has a low accuracy, and deteriorates the reliability of the analysis result. Therefore, the color space conversion process S5 is executed only for the pixels (x, y) for which the value of the flag f (x, y) is set to "1" (i.e., the pixel (x, y) judged to be suitable exposure in the above described effective pixel judgment process S4).

When the color space conversion process S5 is completed, then a lesion judgment process S6 is executed by the lesion judgment unit 222e. The lesion judgment process S6 according to the embodiment of the invention is a process where, for each pixel (x, y) of the endoscopic image, a predicted state (normal, inflammation, ulcer) of a portion corresponding to the pixel is judged depending on which of regions I to III of FIG. 9 described later the pixel (x, y) is plotted in.

Figure 8:
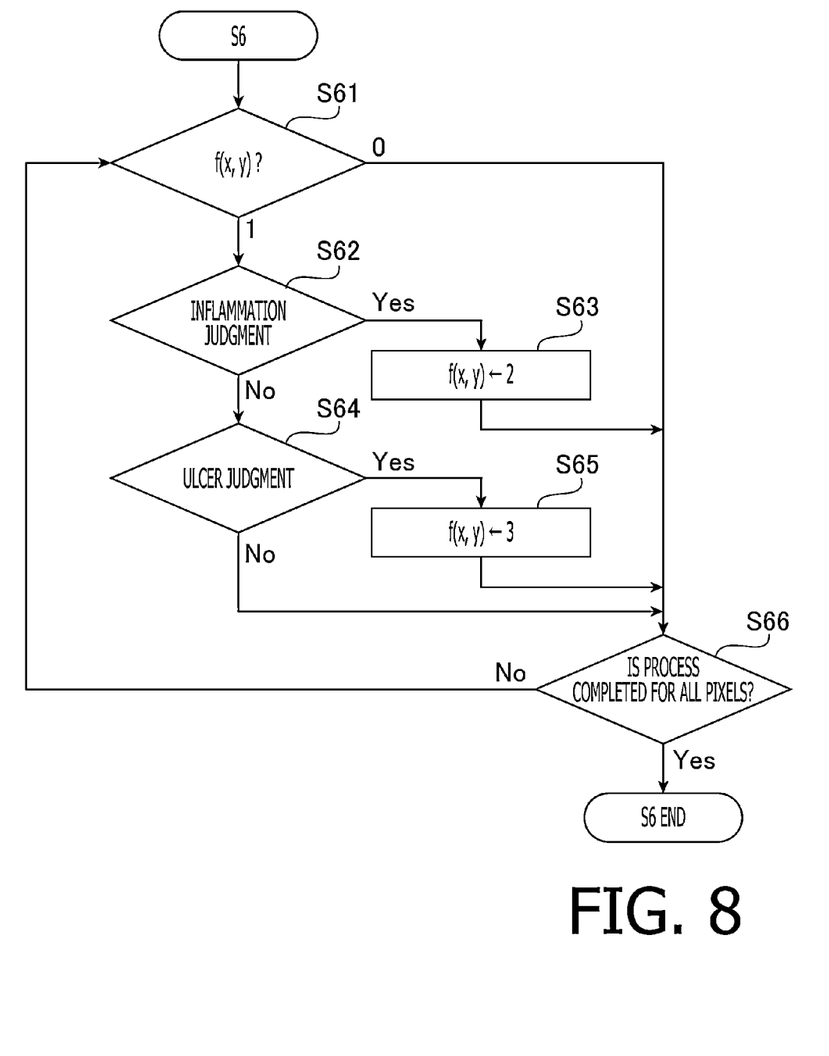
FIG. 8 is a flowchart illustrating a sequence of a lesion judgment process.

FIG. 8 is a flowchart illustrating the sequence of the lesion judgment process S6. The lesion judgment process S6 shown in FIG. 8 is executed sequentially for all the pixels (x, y) constituting the image data. In the lesion judgment process S6, first it is judged whether or not data of each pixel (x, y) is effective with reference to the flag table F (S61). When the value of the flag table f(x, y) is "1" (image data effective), next an inflammation judgment process S62 is executed. When the value of the flag f (x, y) is "0" (image data invalid), the process proceeds to the process S66 without executing the inflammation judgment process S62.

Figure 9:
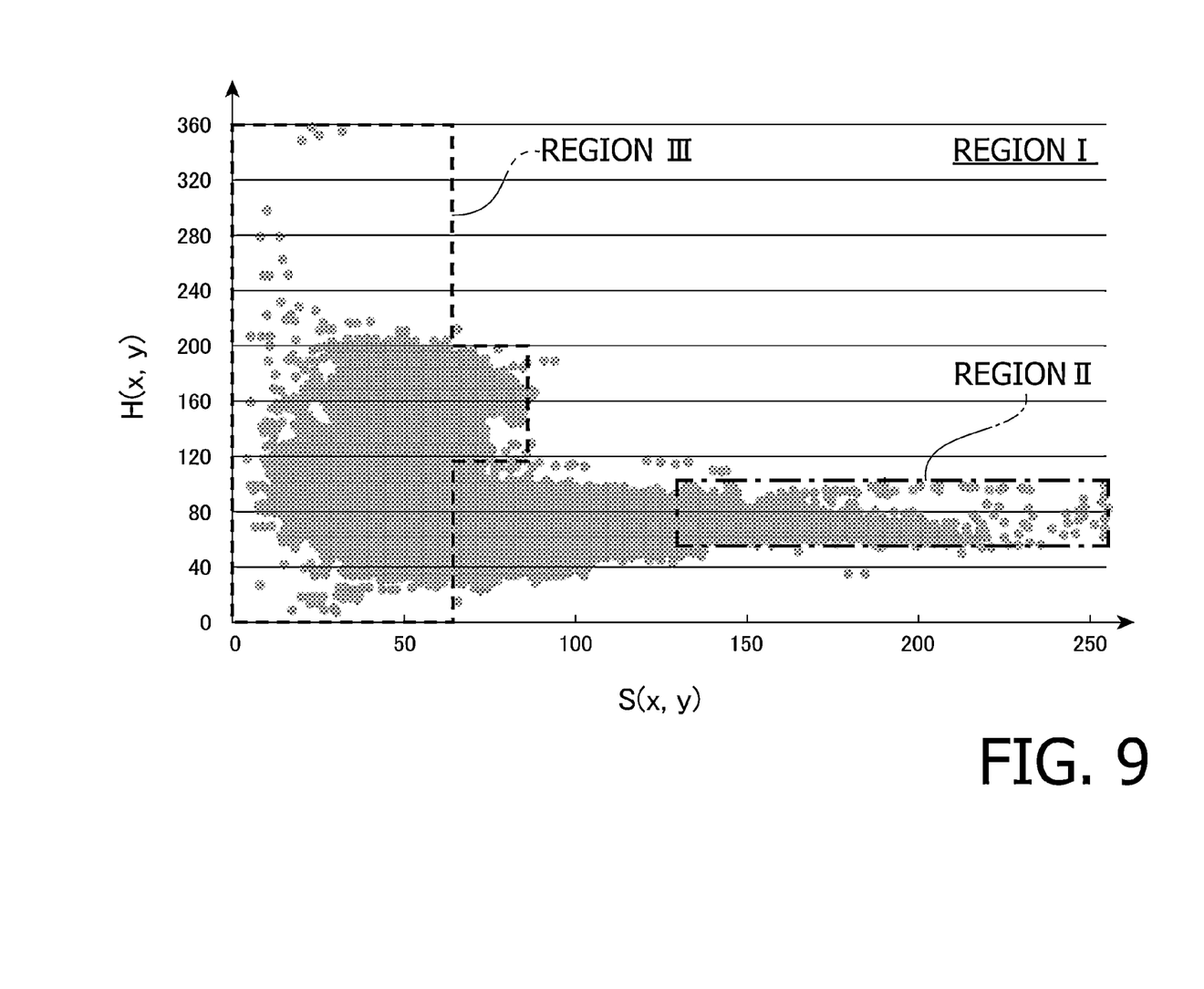
FIG. 9 is a scatter diagram in which pixel values of a living tissue image are plotted in an HS coordinate.

Here, the inflammation judgment process S62 and an ulcer judgment process S64 described later are explained. FIG. 9 is a scatter diagram where the image data (a pair of data composed of hue H(x, y) and saturation S(x, y)) of living tissue images extracted from the endoscope image data of a plurality of inflammatory bowel disease patients are plotted. The scatter diagram of FIG. 9 is divided into a region III which is surrounded by a dashed line on the left side, a region II which is surrounded by a chain line on the lower right side and a region I of the other region. Through the study of the inventors of the present invention, it was founded that a major part of pixels of a portion judged to be an ulcer by an expert doctor in endoscopic diagnosis for the inflammatory bowel disease is plotted in the region III in FIG. 9, and a major part of pixels of a portion judged to be inflammation by the expert doctor is plotted in the region II of FIG. 9, and a major part of pixels of a portion judged to be normal by the expert doctor is plotted in the region I. This means that a state of a living tissue (ulcer or inflammation) can be judged with a high degree of accuracy from two information of hue (tone of a color) and saturation (vividness) of an endoscope observation image obtained by capturing a living tissue.

In the inflammation judgment process S62, it is judged whether or not each pixel value (H(x, y), S(x, y)) is plotted in the region II of FIG. 9. Specifically when the pixel value (H(x, y), S(x, y)) satisfies the following expression 4 and the expression 5, it is judged that the pixel value is plotted in the region II (i.e., it is a pixel of an inflammation portion). It should be noted that $\delta_{H1}$, $\delta_{S1}$, and $\delta_{S2}$ are correction values which can be set by the operator, and, through setting of these correction values, the severity (sensitivity) of the judgment can be adjusted appropriately.

$$130+\delta_{H1} \leq H(x,y) \qquad \text{(Expression 4)}$$

$$60+\delta_{S1} \leq S(x,y) \leq 100+\delta_{S2} \qquad \text{(Expression 5)}$$

When the pixel value (H(x, y), S(x, y)) is plotted in the region II (S62: Yes), the flag f (x, y) corresponding to the pixel (x, y) is rewritten to "2" (inflammation) (S63), and the process proceeds to the process S66. When the pixel value (H(x, y), S(x, y)) is not plotted in the region II (S62: No), an ulcer judgment process S64 is executed subsequently.

In the ulcer judgment process S64, it is judged whether or not the pixel value (H(x, y), S(x, y)) is plotted in the region III of FIG. 9. Specifically, when H(x, y) and S(x, y) satisfy the following expression 6 or the expressions 7 and 8, the pixel value (H(x, y), S(x, y)) is judged to be plotted in the region III (i.e., it is a pixel of an ulcer portion). It should be noted that $\delta_{S3}$, $\delta_{S4}$, and $\delta_{H3}$ are correction values which can be set by the operator, and, through setting of these correction values, the severity (sensitivity) of the judgment can be adjusted appropriately.

$S(x,y) \leq 65+\delta_{S3}$ (Expression 6)

$S(x,y) \leq 85+\delta_{S4}$ (Expression 7)

$120+\delta_{H2} \leq H(x,y) \leq 200+\delta_{H3}$ (Expression 8)

When the pixel value (H(x, y), S(x, y)) is plotted in the region III (S64: Yes), the value of the flag f(x, y) corresponding to the pixel (x, y) is rewritten to "3" (ulcer) (S65), and the process proceeds to process S66. When the pixel value (H(x, y), S(x, y)) is not plotted in the region III (64: No), the pixel is judged to be a normal portion, and the process proceeds directly to the process S66 without rewriting the value "1" of the flag f (x, y).

In the process S66, it is judged whether or not the process is completed for all the pixels (x, y). Until the process is completed for all the pixels (x, y), the above described processes S61 to S66 are repeated.

When the lesion judgment process S6 is completed, next the overlay process S7 according to the embodiment of the invention is executed by the overlay process unit 222f. The overlay process S7 is a process where, for the pixel judged to be a lesion portion such as inflammation or an ulcer by the lesion judgment process S6, the color is changed to have a color tone associated with the lesion (the flag value) so that the pixel can be distinguished from an pixel judged to be normal (not having a lesion). In this embodiment, a process where red color is enhanced (specifically, a red component is increased) for the pixel judged to be an ulcer and yellow color is enhanced (specifically, green and blue components are enhanced) for a pixel judged to be inflammation is executed.

Figure 10:
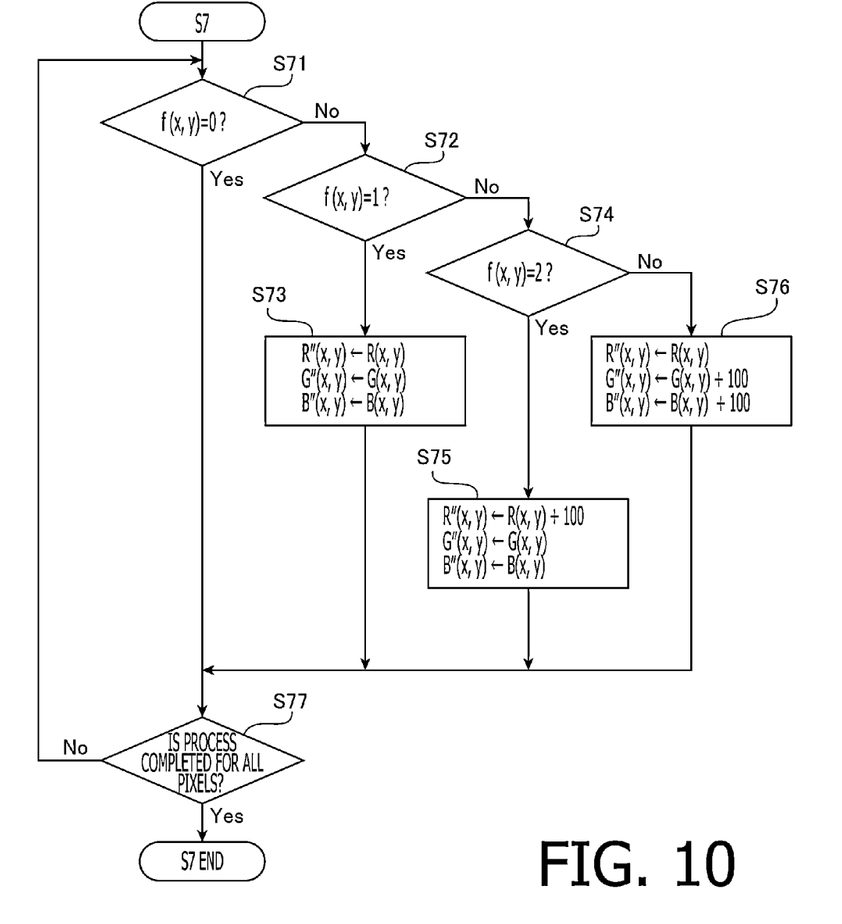
FIG. 10 is a flowchart illustrating a sequence of an overlay process.

FIG. 10 is a flowchart illustrating a sequence of the overlay process S7. The overlay process S7 shown in FIG. 10 is executed sequentially for all the pixels (x, y) constituting the normal observation image data N. In the overlay process S7, first the value of the flag f(x, y) corresponding each pixel (x, y) is judged with reference to the flag table F (S71, S72, S74). When the value of the flag is "0" (image data invalid) (S71: Yes), the process proceeds directly to the process S77. When the value of the flag f(x, y) is "1" (normal) (S71: No, S72: Yes), the primary color signals R(x, y), G(x, y), B(x, y) of the normal observation image data N are defined as the primary color signals R"(x, y), G"(x, y), B"(x, y) of the overlay image data S without change (S73), and the process proceeds to the process S77. When the value of the flag f(x, y) is "2" (inflammation) (S71: No, S72: No, S74: Yes), a value obtained by adding 100 to the value of the primary color signal R(x, y) of the normal observation image data N is defined as the primary color signal R"(x, y) of the overlay image data S, and the primary color signals G(x, y) and B(x, y) of the normal observation image data N are defined as the primary color signals G"(x, y) and B"(x, y) of the overlay image data S without change (S75), and the process proceeds to the process S77. When the value of the flag f(x, y) is "3" (ulcer) (S71: No, S72: No S74: No), a value obtained by adding 100 to the primary color signals G(x, y) and B(x, y) of the normal observation image data N are defined as the values of the G"(x, y) and B"(x, y) of the overlay image data S, and the primary color signal R(x, y) of the normal observation image data N is defined as the primary color signal R"(x, y) of the overlay image data S without change (S76), and the process proceeds to the process S77. Here, although in this embodiment the three primary color signals R, G, B of the normal observation image data N are used for the overlay process S7, in another embodiment primary color signals R'(x, y), G'(x, y), B'(x, y) of the tone enhanced image data E may be used.

In the process S77, it is judged whether the process is completed for all the pixels (x, y). Until the process is completed for all the pixels (x, y), the above described processes S71 to S77 are repeated.

When the overlay process S7 is completed, the overlay image data S generated by the overlay process S7 is output to the image memory 224, and are stored in the overlay image memory areas 0sR, 0sG, 0sB (k=0 to 6), respectively.

Next, a judgment S8 (FIG. 5) on whether or not an instruction for storing a still image is issued is executed. When the image processing unit 220 receives the position information Pos of the tip part of the electronic scope 100 together with the instruction for storing a still image from the driver signal processing circuit 112 (S8: Yes), the image processing unit 220 stores copies of the normal observation image data N, the tone enhanced image data E and the overlay image data S stored in the memory area groups P0 of the image memory 224 in one of the memory area groups P1 to P6 corresponding to the position information Pos (S9). Then, the screen display process S10 is executed. When the instruction for storing a still image is not received from the driver signal processing circuit 112 (S8: No), the process proceeds to the screen display process S10 without executing the process S9.

The next screen display process S10 is a process where the display screen data for displaying on the monitor 300 is generated and is converted into a video signal and is output, and is executed by the display screen generating unit 228a of the second image processing circuit 228. The display screen generating unit 228a is able to generate a plurality of types of display screen data in accordance with control by the system controller 202.

Figure 11:
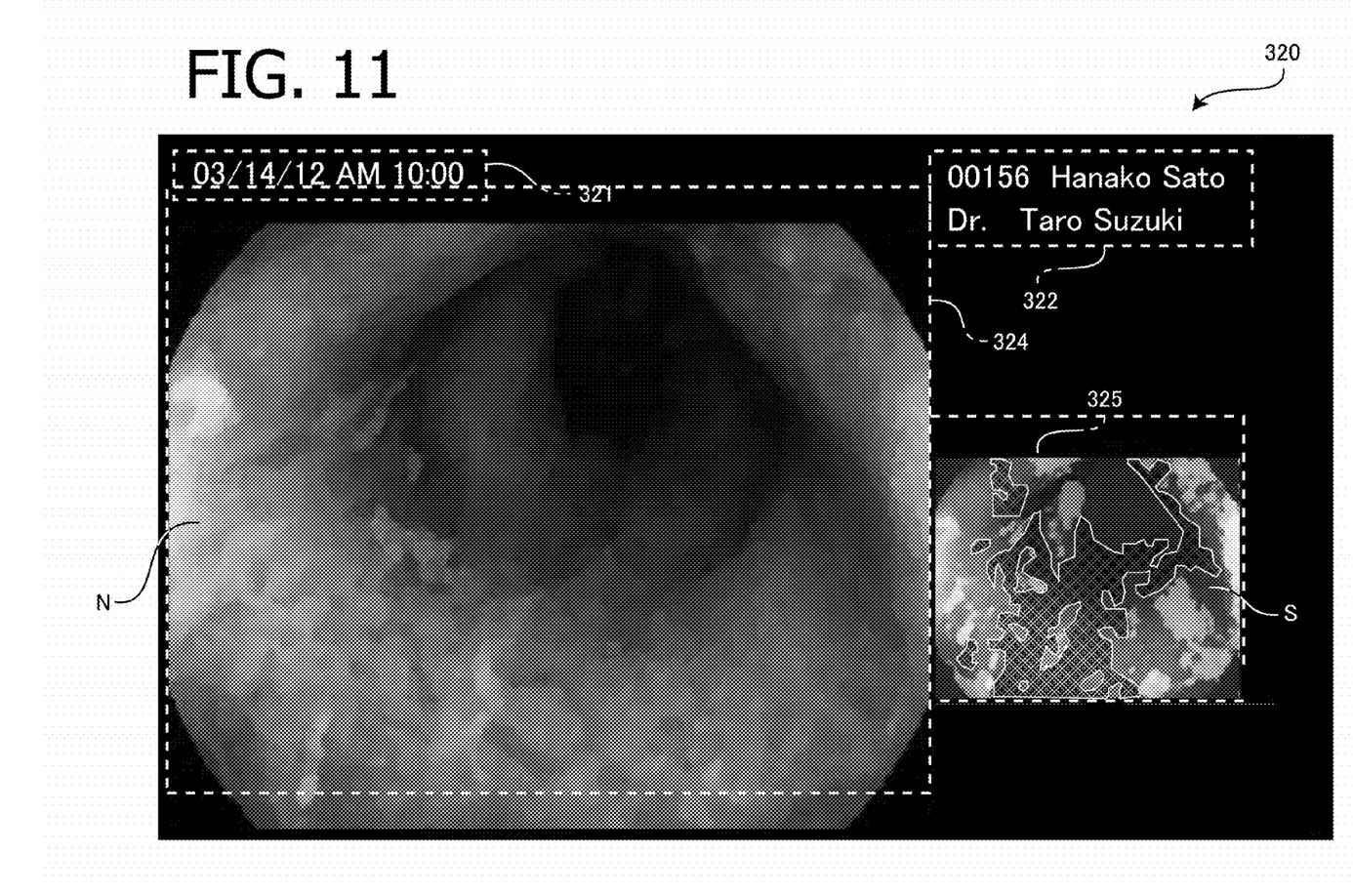
FIG. 11 is an example of a display screen generated by a screen display process.

FIG. 11 is an example of a display screen generated by the screen display process S10, and is an analysis mode observation screen 320 displayed during endoscopic observation in the image analysis mode. The analysis mode observation screen 320 includes a date and time display area 321 on which date and time of image capturing is displayed, a basic information display area 322 on which basic information concerning diagnosis (e.g., a medical record number, a patient name and an operator name) is displayed, a normal image display area 324 on which the normal observation image data N (or the tone enhanced image data E) is displayed, and an analysis image display area 325 on which the overlay image data S (the observation image after the overlay process S7) is displayed.

In the screen display process S10, the display screen generating unit 228a reads the real time normal observation image data N and the overlay image data S from the memory area group P0 of the image memory 224, and displays them on the normal image display area 324 and the analysis image display area 325, respectively. Furthermore, on the date and time display area 321 and the basic information display area 322, information provided by the system controller 202 is displayed.

The operator conducts the endoscopic observation while viewing the analysis mode observation screen 320. Specifically, the operator conducts the endoscopic observation while viewing the normal observation image data N (or the tone enhanced image data E) displayed on the normal image display area 324 and while referring to the overlay image data S displayed on the analysis image display area 325. By carefully observing particularly for a colored portion on the overlay image data S, it becomes possible to conduct accurate diagnosis without overlooking a lesion portion.

Next, it is judged whether or not the endoscopic observation should continue (S11). The above described processes S1 to S11 are repeated until a user operation for instructing stop of endoscopic examination or stop of operation of the electronic endoscope device 1 is conducted to the operation panel 208 of the processor 200 for an electronic endoscope (S11: No).

The forgoing is the explanation about the embodiment; however, the invention is not limited to the above described embodiment but can be varied within the scope of the technical concept expressed by the claims.

Although, in the above described embodiment, judgment on a lesion is made in the HSI space, judgment on a lesion may be made in the HSV (HSB) space based on Hue, Saturation and Value (or Brightness) in place of HSI space.

In the above described embodiment, the TE process S3 is executed in the RGB space; however, the TE process S3 may be executed in the HSI space after the color space conversion process S5.

In the above described embodiment, the configuration where the information on the position of the tip part of the electronic scope 100 (the image capturing position) is obtained using the optical sensor 132; however, the invention is not limited to such a configuration, and a configuration where the information on the image capturing position is obtained by another means may be employed. For example, a configuration where an optical proximity sensor having a light source and a light-receiving element are provided in the insertion unit 130 of the electronic scope 100 in place of the optical sensor 132 may be employed. In this case, when the optical proximity sensor is inserted in to a digestive tube, light reflected from the inner wall of the digestive tube is detected by the light-receiving element, and proximity is detected. Therefore, in contrast to the above described embodiment, by judging that the distribution length of the optical proximity-sensors whose light-receiving elements are receiving light is the length of the insertion unit 130 being inserted into the digestive tube, the information on the position of the tip part of the electronic scope 100 can be obtained.

A configuration where a moving amount sensor which detects the moving amount (the distance and the direction of movement) by the same principle as that of an optical mouse is provided in the insertion unit 130 of the electronic scope 100 in place of the optical sensor 132 may be employed. In this case, only one moving amount sensor may be provided close to the tip of the insertion unit 130.

It should be noted that, as a light source of the optical proximity-sensor or the moving amount sensor, a light source (LD or LED) of a wavelength within near infrared to a visible light region may be used, however, by using a light source of a red light region having a high degree of reflectivity on a living tissue surface, a high degree of detection accuracy can be obtained.

Furthermore, by obtaining a magnetic resonance image, an X-ray image or an ultrasonic image from the outside of a patient body during endoscopic examination, the position of the tip part of the electronic endoscope may be determined from these images. Furthermore, by calculating the moving amount of the tip part of the endoscope in a digestive tract through image analysis of an endoscopic image, the position of the tip part of the endoscope may be determined.

The above described embodiment is an example in which the invention applied to endoscopic examination for inflammatory diseases; however, as a matter of course, the invention may be applied to endoscopic examination for another disease.

Although the above described embodiment is configured such that a still image is recorded by a manual operation by an operator, a configuration where the driver signal processing circuit 112 automatically issues an instruction for storing a still image and automatically storing a still image when the tip part of the insertion unit 130 reaches a predetermined still image obtaining position (an observation point) while the insertion unit 130 of the electronic scope 100 is pulled out from the deepest portion of an examination area.

In the above described embodiment, a CCD image sensor is used as the solid state image pickup device 108; however, a configuration where a solid state image pickup device having a different configuration, such as a CMOS (Complementary Metal Oxide Semiconductor), is used may be employed.

In the above described embodiment, the solid state image pickup device 108 having the RGB bayer array color filter 108b is used; however, a configuration having a solid state image pickup device having a complementary color filter of Cy (Cyan), Mg (Magenta), Ye (Yellow) and G (Green) may be employed.

What is claimed is:

1. An image processing device, comprising:
   an obtainer that obtains color endoscopic image data;
   a color space converter that converts, by a processor, a color space of the color endoscopic image data to one of an HSI color space based on hue, saturation and intensity, and an HSV color space based on hue, saturation and value;
   a lesion pixel judger that judges, by a processor, for each of pixels constituting a color endoscopic image, whether or not each pixel is a lesion portion based on the hue and the saturation in the converted color space;
   an overlay processor that executes an overlay process which changes a color of the pixel judged to be the lesion portion by the lesion pixel judger, the overlay processor changes the color of the pixel judged to be the lesion portion by enhancing a predetermined color component of the pixel judged to be the lesion portion and not enhancing the predetermined color component of a pixel not judged to be the lesion portion; and
   an overlay image display that displays an overlay image obtained by subjecting the color endoscopic image to the overlay process,
   wherein each of the obtainer, the converter, the judger the overlay processor and the display comprise an image processing circuit.

2. The image processing device according to claim 1, wherein:
   the lesion pixel judger judges whether or not each pixel is a pixel of the lesion portion, for each of a plurality of types of lesions; and
   the overlay processor changes a color of the pixel of the lesion portion depending on a type of lesion.

3. The image processing device according to claim 2, wherein the overlay processor adds a predetermined value corresponding to a type of lesion to a pixel value of a pixel judged to be the lesion portion.

4. The image processing device according to claim 1, wherein the overlay image display concurrently displays the color endoscopic image and the overlay image.

5. The image processing device according to claim 1,
   further comprising an effective pixel judger that judges, for each of the pixels constituting the color endoscopic image, whether or not each pixel is effective by judging whether or not a pixel value is within a predetermined range; and the lesion pixel judger judges whether each pixel is a pixel of the lesion portion for the pixel judged to be effective by the effective pixel judger.

6. The image processing device according to claim 1, further comprising a tone enhancer that executes a tone enhancement process that applies a non-linear gain to a pixel value so that a dynamic range near a boundary of a region of the pixel value for which the pixel is judged to be the lesion portion is broadened, wherein the lesion pixel judger makes a judgment based on the pixel value after the tone enhancement process.

7. The image processing device according to claim 6, wherein the color endoscopic image data is converted into the HSI color space or the HSV color space after being subjected to the tone enhancement process in the color space of the color endoscopic image.

8. The image processing device according to claim 7, wherein the tone enhancer executes the tone enhancement process while applying different gain curves to intensity values of respective primary colors of R, G and B.

9. The image processing device according to claim 1, wherein the lesion includes an inflammation and an ulcer in an inflammatory bowel disease.

10. An endoscope device, comprising:
an image processing device according to claim 1; and
an endoscope that generates the color endoscopic image data and outputs the color endoscopic image data to the image processing device.

11. The image processing device according to claim 1, further comprising a tone enhancer that executes a tone enhancement process that applies a non-linear gain to a pixel value and executes the tone enhancement process while applying different gain values to intensity values of the respective primary colors R, G and B.

12. The image processing device according to claim 1, wherein the color endoscopic image data comprises luminance signals and color difference signals converted, by an RGB conversion matrix, into primary color signals.

13. The image processing device according to claim 1, further comprising an effective pixel judger that judges whether or not each pixel is suitable, based upon whether a pixel value is within a predetermined exposure range, and the color space converter converts the color space of the color endoscopic image data for each pixel within the suitable exposure range.

14. The image processing apparatus according to claim 1, wherein the lesion pixel judger judges whether or not each pixel is a lesion portion based upon whether the hue and saturation of the pixel falls within predetermined ranges.

* * * * *